United States Patent
Carter et al.

(10) Patent No.: US 7,124,762 B2
(45) Date of Patent: Oct. 24, 2006

(54) DOVETAIL MENISCAL ALLOGRAFT TECHNIQUE AND SYSTEM

(75) Inventors: Thomas R. Carter, Paradise Valley, AZ (US); Reinhold Schmieding, Naples, FL (US); Donald K. Shuler, Naples, FL (US)

(73) Assignee: Arthrex, Inc., Naples, FL (US)

( * ) Notice: Subject to any disclaimer, the term of this patent is extended or adjusted under 35 U.S.C. 154(b) by 71 days.

(21) Appl. No.: 10/640,300

(22) Filed: Aug. 14, 2003

(65) Prior Publication Data

US 2004/0034419 A1    Feb. 19, 2004

Related U.S. Application Data

(60) Provisional application No. 60/403,438, filed on Aug. 15, 2002.

(51) Int. Cl.
*A61B 19/00* (2006.01)
*A61B 5/00* (2006.01)
*A61F 2/08* (2006.01)

(52) U.S. Cl. .................. 128/898; 623/14.12; 606/86
(58) Field of Classification Search ................ 128/898; 623/14.12, 13.11, 13.12; 606/86–88, 79–85, 606/96

See application file for complete search history.

(56) References Cited

U.S. PATENT DOCUMENTS 3,973,277 A * 8/1976 Semple et al. ........... 623/13.14
4,597,766 A * 7/1986 Hilal et al. ............... 623/13.17
6,077,989 A * 6/2000 Kandel et al. ........... 623/13.17
6,102,954 A * 8/2000 Albrektsson et al. .... 623/20.32
6,299,645 B1 * 10/2001 Ogden ..................... 623/20.21
6,511,509 B1 * 1/2003 Ford et al. ................ 623/23.5
6,699,252 B1 3/2004 Farr, II et al.
2002/0082703 A1 * 6/2002 Repicci ................... 623/20.29

OTHER PUBLICATIONS

Albee, Fred H., "Bone Graft Surgery in Disease, Injury and Deformity" 1940; pp. 30, 196-198.*
Arthrex, Meniscal Allograft "Keyhole" Surgical Technique, 2003.
CryoLife, Inc., Keyhole Meniscus Reconstruction Surgical Technique.

* cited by examiner

Primary Examiner—David J Isabella
(74) Attorney, Agent, or Firm—Dickstein Shapiro LLP (57) ABSTRACT

A meniscal allograft with a bone block having a trapezoidal shape in cross-section and a technique for using a meniscus allograft having a trapezoidal shaped bone block are disclosed. A groove is formed initially in the bone using drill bits. Dilators are used to increase the size of the drilled groove. The orthogonal corner at the bottom of the groove is shaped using a rasp. A smooth dilator compacts the bone in the acute angle at the bottom of the groove opposite the orthogonal corner to create the final trapezoid shape of the bone groove. A meniscal allograft having a bone block of corresponding trapezoidal shape is prepared using a workstation and three cutting jigs to make three corresponding cuts. The trapezoidal bone block of the meniscal allograft is then installed within the bone groove.

4 Claims, 15 Drawing Sheets

FIG. 32 though the "keyhole" technique
DOVETAIL MENISCAL ALLOGRAFT TECHNIQUE AND SYSTEM This application claims the benefit of U.S. Provisional Application Ser. No. 60/403,438, filed Aug. 15, 2002, the entire disclosure of which is incorporated herein by reference.

FIELD OF THE INVENTION

The present invention relates to the field of surgery reconstruction and, in particular, to a meniscal allograft technique and system using a meniscal allograft having a dovetail notch.

BACKGROUND OF THE INVENTION

A known method of performing an anatomical reconstruction of the meniscus is the so-called meniscal allograft "keyhole" technique using instrumentation sold by Arthrex, Inc. of Naples, Fla. In this technique, the bone block of a meniscal allograft is formed in the shape of a keyhole plug, to match a corresponding keyhole groove prepared through the cortical and cartilagenous surface of the tibial plateau. The bone plug for the meniscal allograft is then fed into the keyhole groove, such that the meniscal allograft is mounted on the tibial plateau and secured without transosseous sutures.

Although the above-described technique is a vast improvement over prior meniscal allograft technique, the "keyhole" shape of the allograft implant is difficult to reproduce and necessitates a long preparation time, typically about 45 minutes. Thus, although the "keyhole" technique described above is a vast improvement over prior meniscal allograft techniques, it would be desirable to provide a meniscal transplant system and technique that is quicker, easier and more reproducible.

SUMMARY OF THE INVENTION

The present invention overcomes the disadvantages of the "keyhole" technique by providing a meniscal allograft technique using a meniscus allograft having a trapezoidal shape in cross-section, as opposed to a "keyhole" shape. The trapezoidal shape is more easily reproducible than a "keyhole" shape. Preferably, the dovetail meniscus allograft has a trapezoidal shape with a 90 degree angle and is formed as a pre-cut meniscal allograft.

The dovetail meniscus allograft of the present invention is advanced into a same-size dovetail groove of a bone by impaction. The dovetail groove is formed initially using drill bits. Dilators are used to increase the size of the drilled openings. The orthogonal corner at the bottom of the groove is shaped using a rasp. A smooth dilator compacts the bone in the acute angle at the bottom of the groove opposite the orthogonal corner to create the final dovetail shape.

These and other features and advantages of the invention will be more apparent from the following detailed description that is provided in connection with the accompanying drawings and illustrated exemplary embodiments of the invention.

DETAILED DESCRIPTION OF THE INVENTION

The present invention provides a meniscal allograft technique for forming a longitudinal groove in a bone, the groove having a trapezoidal or dovetail cross-section, and providing a pre-cut meniscal allograft also having a trapezoidal or dovetail cross-section. The trapezoidal shape of the pre-cut meniscal allograft is more easily reproducible than a "keyhole" shape.

Figure 31:
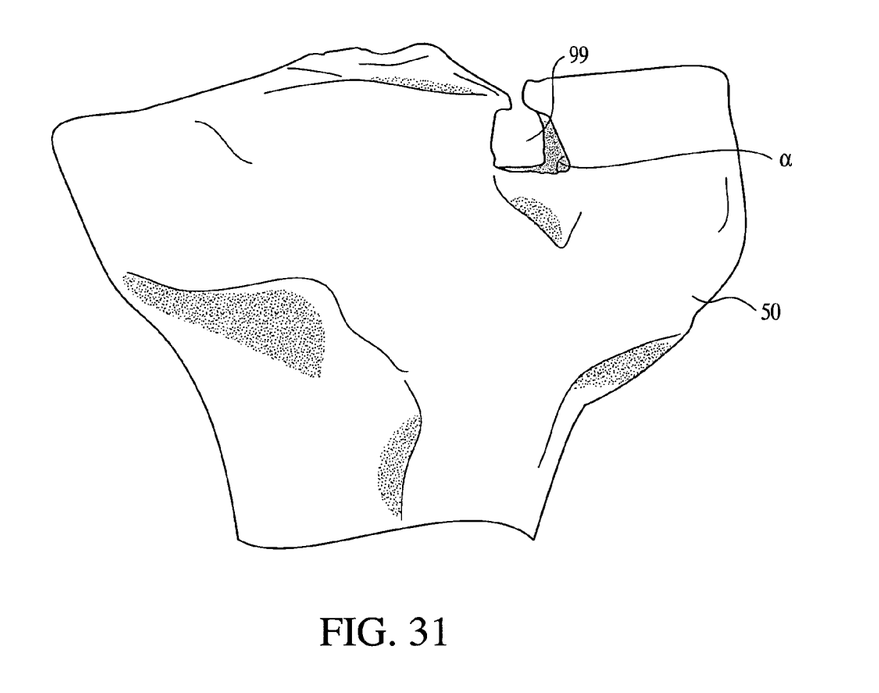
FIG. 31 illustrates another view of the dovetail tibial groove of FIG. 30.
Figure 32:
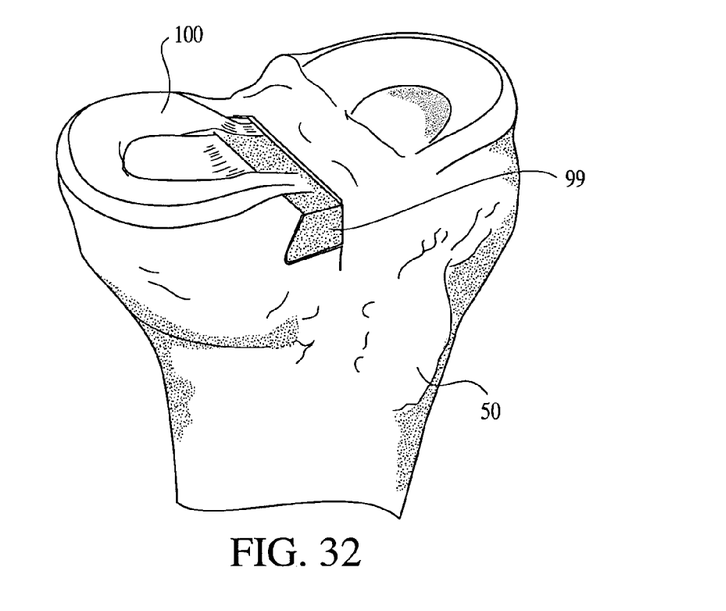
FIG. 32 illustrates the dovetail allograft implant of FIGS. 15–17 inserted into the dovetail tibial groove of FIG. 31.

Referring now to the drawings, where like elements are designated by like reference numerals, FIGS. 1–17 illustrate an exemplary embodiment of a dovetail meniscal allograft implant 100 (FIGS. 15–17) fabricated according to the present invention, while FIGS. 18–31 illustrate the formation of a longitudinal dovetail tibial groove 99 (FIG. 31) that accommodates the dovetail meniscal allograft implant 100. FIG. 32 illustrates the dovetail meniscal allograft implant 100 of FIGS. 15–17 inserted into the dovetail tibial groove 99 of FIG. 31.

The dovetail meniscus implant 100 can be machined from allograft cortical bone using known techniques, and is preferably a single piece of harvested material with the meniscus on a bone block. Alternatively, the implant can be formed of a synthetic material, preferably a synthetic cortical bone material. A preferred synthetic bone material is tricalcium phosphate (TCP) and/or hydroxyapatite (HA), or a biodegradable polymer, preferably a polylactide, such as PLLA.

Figure 1:
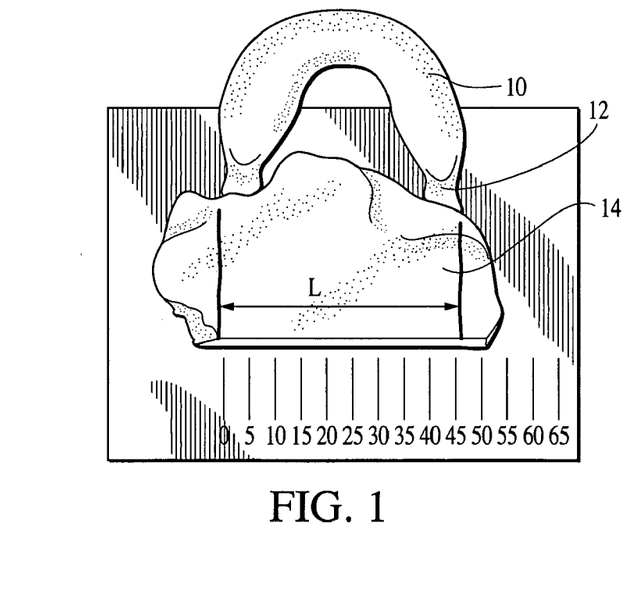
FIG. 1 illustrates an exemplary dovetail allograft implant according to the present invention at an initial stage of fabrication.
Figure 2:
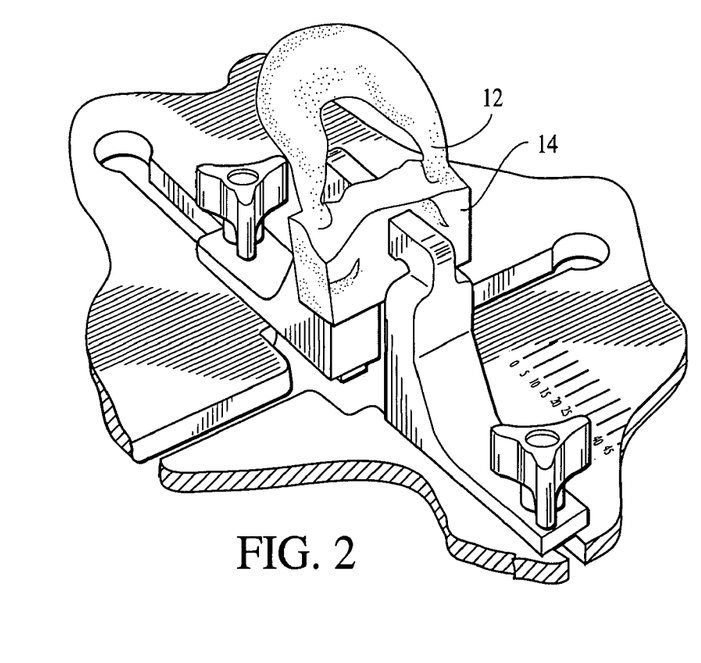
FIG. 2 illustrates the dovetail allograft implant of FIG. 1 at a stage of fabrication subsequent to that shown in FIG. 1.
Figure 3:
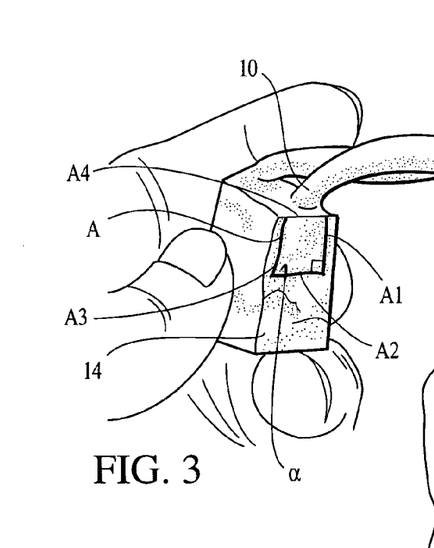
FIG. 3 illustrates the dovetail allograft implant of FIG. 1 at a stage of fabrication subsequent to that shown in FIG. 2.

FIG. 1 illustrates a meniscus 10 formed of allograft cortical bone. As shown in FIG. 1, meniscus 10 is first mounted on a graft workstation, where bone block 14 is marked and trimmed to a length "L" corresponding to the longitudinal length of dovetail tibial groove 99 (the formation of which will be described in more detail below with reference to FIGS. 17–30). Referring to FIG. 2, any additional bone that is anterior or posterior to the sides of horns 12 of meniscus 10 is removed. FIG. 3 shows the marking of dovetail configuration A onto both the anterior and posterior facets of the bone block 14, so that the horns 12 are centered on side $A_4$ of the trapezoid or dovetail configuration A. The dovetail configuration A is a cross-sectional trapezoidal shape with four edges $A_1$ (height), $A_2$ (base), $A_3$ and $A_4$ (small base), edges $A_1$ and $A_2$ forming a ninety degree angle and edges $A_2$ and $A_3$ forming an acute dovetail angle α, as shown in FIG. 3. The acute dovetail angle α is about 25 degrees to about 75 degrees, more preferably about 45 degrees.

Figure 4:
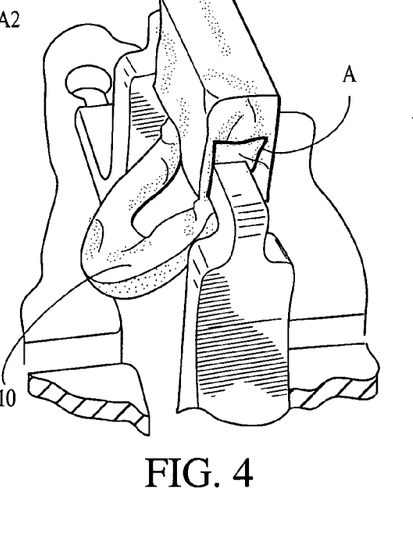
FIG. 4 illustrates the dovetail allograft implant of FIG. 1 at a stage of fabrication subsequent to that shown in FIG. 3.
Figure 5:
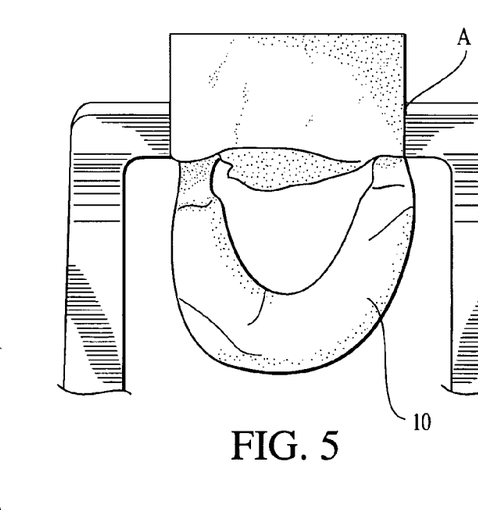
FIG. 5 illustrates another view of the dovetail allograft implant of FIG. 5.

FIGS. 4 and 5 illustrate meniscus 10 secured between two grafting holding posts and positioned upside down. As shown in FIGS. 4 and 5, meniscus 10 hangs freely and away from the bone block 14, so that the edge $A_1$ of the dovetail configuration A is aligned with the holding posts. As also illustrated in FIG. 4, base $A_2$ is aligned with the bottom of the holding posts.

Figure 6:
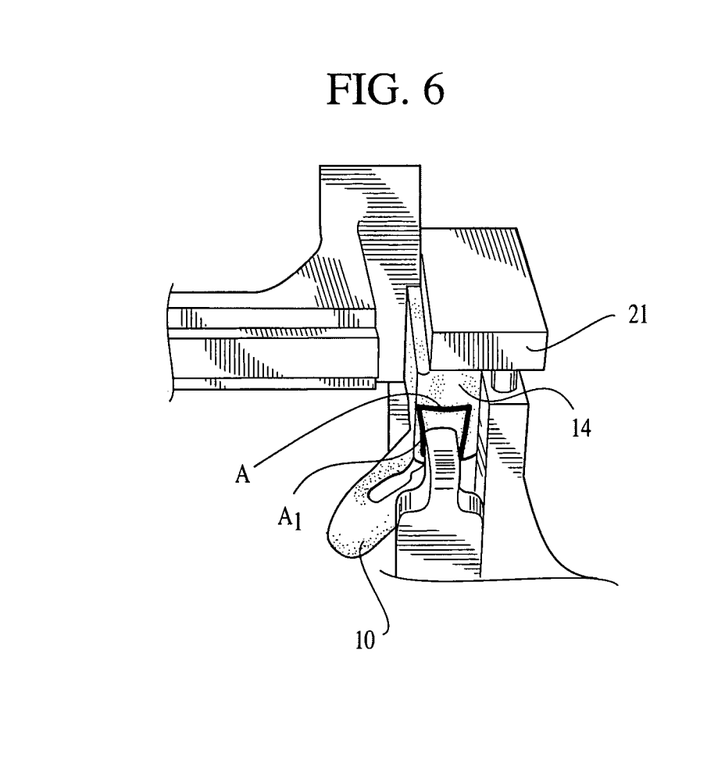
FIG. 6 illustrates the dovetail allograft implant of FIG. 1 at a stage of fabrication subsequent to that shown in FIG. 4.
Figure 7:
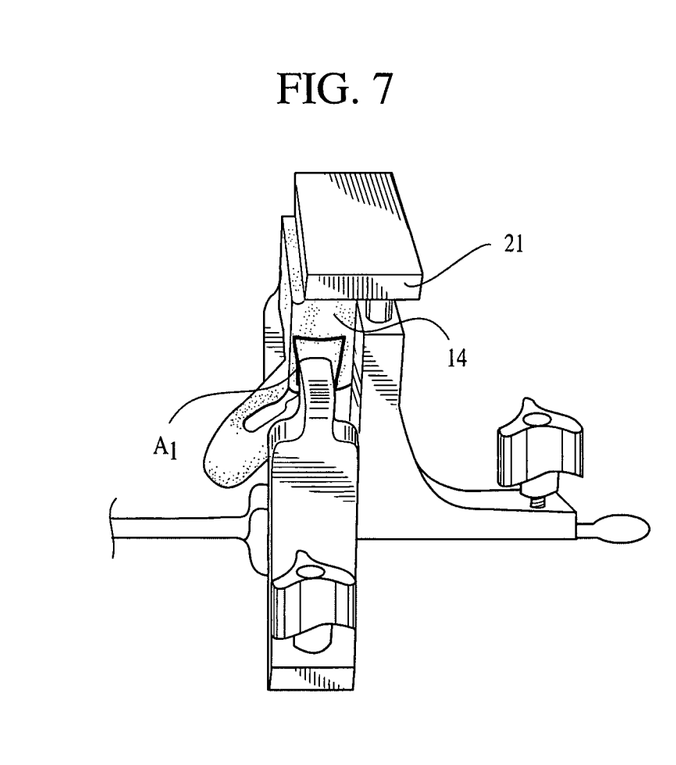
FIG. 7 illustrates the dovetail allograft implant of FIG. 1 at a stage of fabrication subsequent to that shown in FIG. 6.
Figure 8:
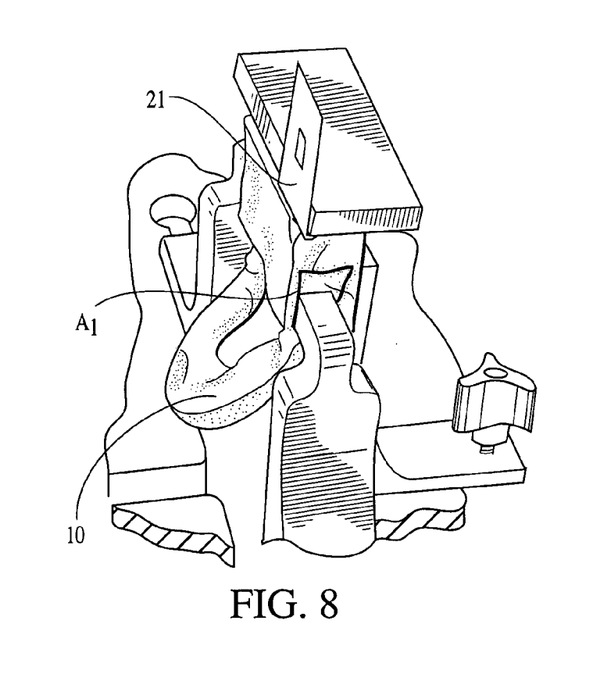
FIG. 8 illustrates the dovetail allograft implant of FIG. 1 at a stage of fabrication subsequent to that shown in FIG. 7.
Figure 9:
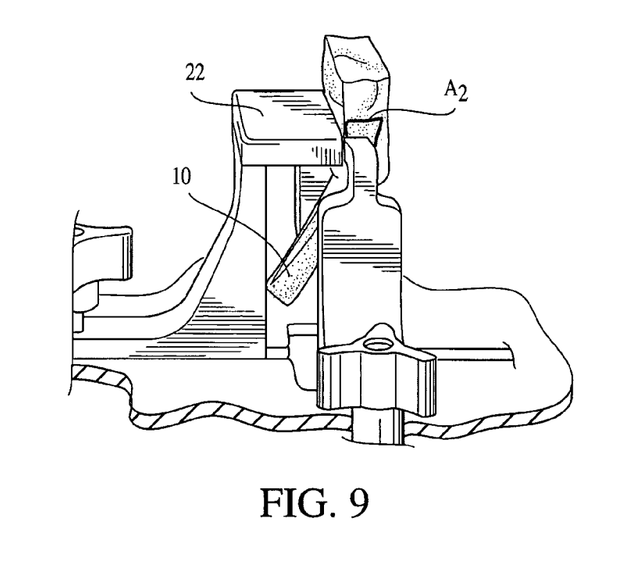
FIG. 9 illustrates the dovetail allograft implant of FIG. 1 at a stage of fabrication subsequent to that shown in FIG. 8.
Figure 10:
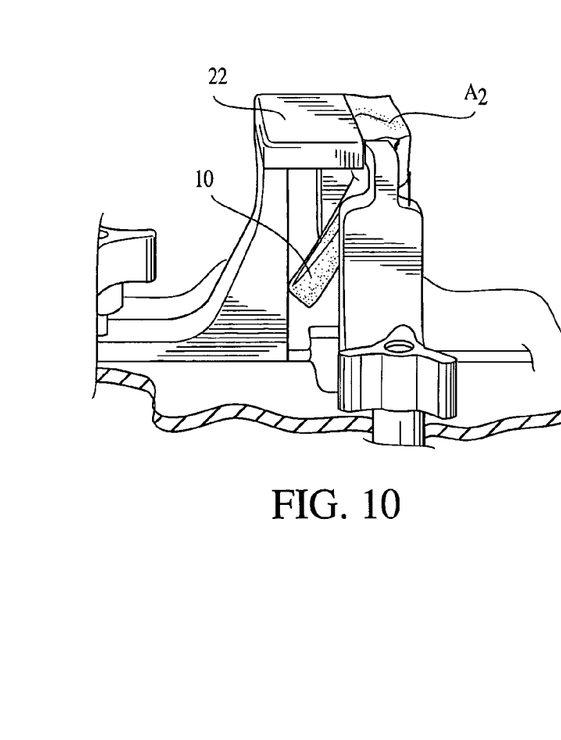
FIG. 10 illustrates the dovetail allograft implant of FIG. 1 at a stage of fabrication subsequent to that shown in FIG. 9.
Figure 11:
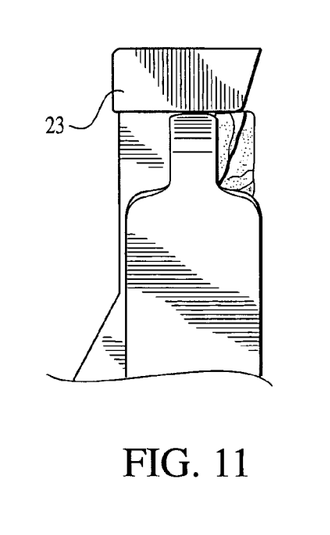
FIG. 11 illustrates the dovetail allograft implant of FIG. 1 at a stage of fabrication subsequent to that shown in FIG. 10.
Figure 12:
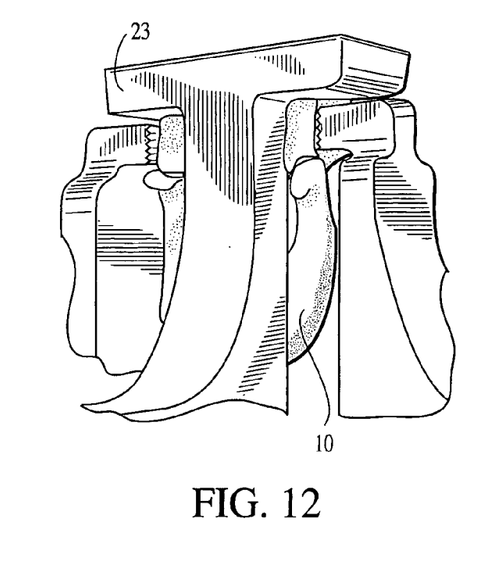
FIG. 12 illustrates another view of the dovetail allograft implant of FIG. 11.
Figure 13:
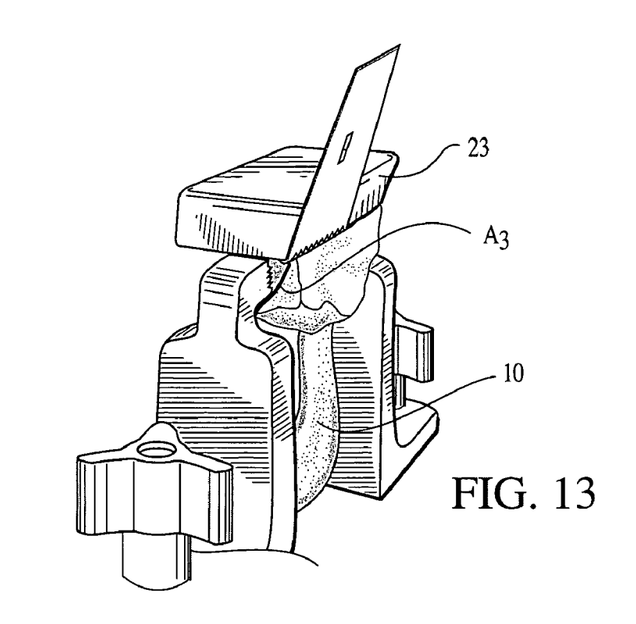
FIG. 13 illustrates the dovetail allograft implant of FIG. 1 at a stage of fabrication subsequent to that shown in FIG. 11.
Figure 14:
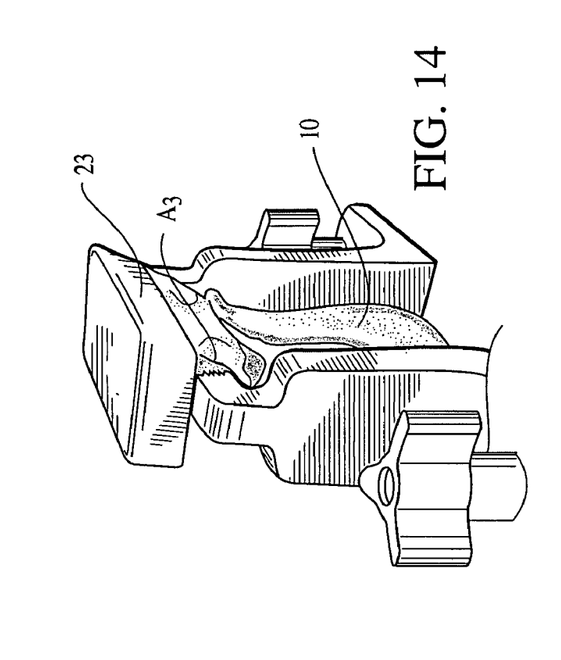
FIG. 14 illustrates the dovetail allograft implant of FIG. 1 at a stage of fabrication subsequent to that shown in FIG. 13.

Referring now to FIGS. 6–8, a first cutting jig 21 is aligned (FIGS. 6, 7) to the edge $A_1$ of the of the meniscus 10, so that bone from the bone block 14 is vertically cut (FIG. 8) along the edge $A_1$ of the dovetail configuration A. A second cutting jig 22 (FIG. 9) is then aligned with the flat base $A_2$ so that bone from the block 14 is horizontally cut along the base $A_2$ of the dovetail configuration A of the bone block 14, as shown in FIG. 10. The length of the edge $A_1$ of the dovetail configuration A is of about 8 mm to about 12 mm, more preferably of about 10 mm. The length of the base $A_2$ of the dovetail configuration A is of about 8 mm to about 12 mm, more preferably of about 10.5 mm.

Figure 15:
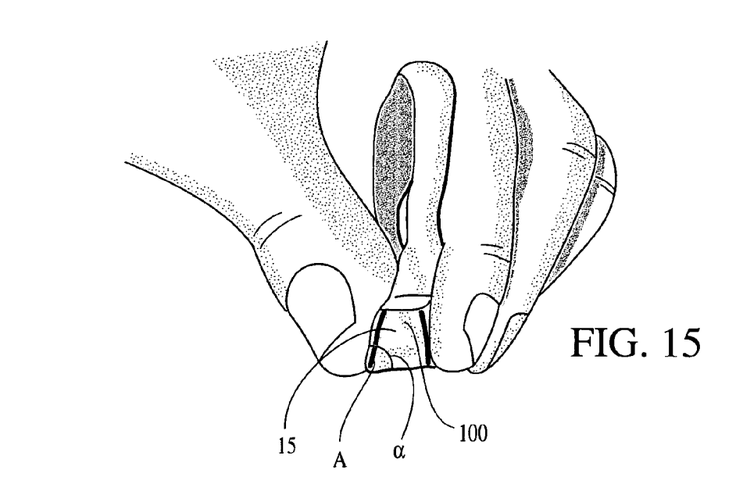
FIG. 15 illustrates the dovetail allograft implant of FIG. 1 at a stage of fabrication subsequent to that shown in FIG. 14.
Figure 16:
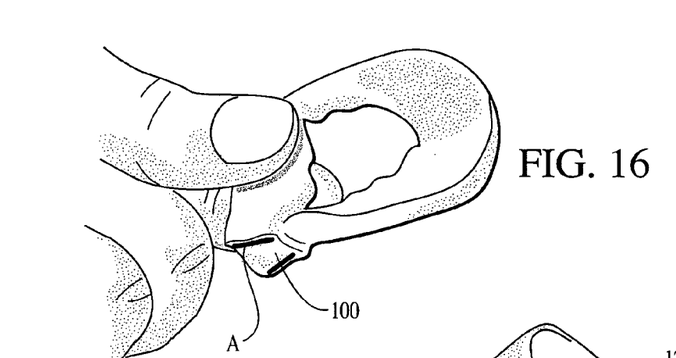
FIG. 16 illustrates another view of the dovetail allograft implant of FIG. 15.
Figure 17:
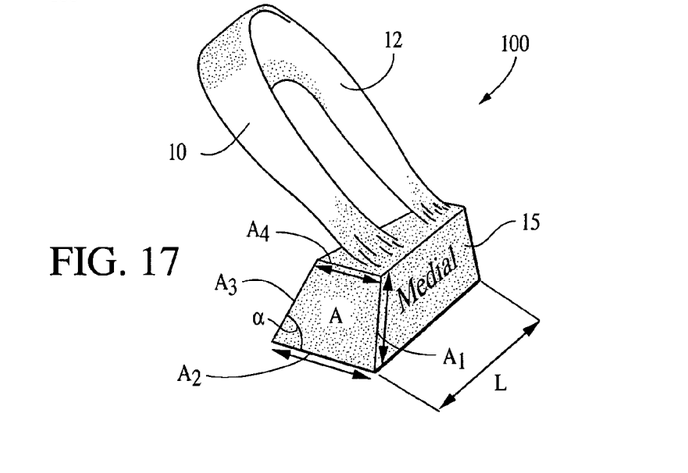
FIG. 17 illustrates yet another view of the dovetail allograft implant of FIG. 15.

FIGS. 11–14 illustrate cutting of bone from the bone block 14 along edge $A_3$ of the dovetail configuration A using a third cutting jig 23, to define the length of the edge or small base $A_4$ and to complete the fabrication of body 15 of the dovetail meniscal allograft implant 100. The length of the small base $A_4$ is of about 5 mm to about 10 mm, more preferably of about 7 mm. As illustrated in FIGS. 15, 16 and 17, which are more detailed illustrations of the dovetail meniscal allograft implant 100 fabricated as described above, body 15 is defined by the four edges ($A_1$, $A_2$, $A_3$ and $A_4$) of the dovetail or trapezoid configuration A, with the horns 12 of the meniscus 10 attached to the surface defined by the small base $A_4$ and the length L of the body 15.

A method of forming longitudinal dovetail tibial groove 99 (FIG. 30) is now described with reference to FIGS. 18–31 and by using known techniques of drilling through the tibia 50, shown in FIG. 18. The longitudinal tibial groove 99 of the present invention has a dovetail configuration and a size that accommodates the insertion of the dovetail meniscal allograft implant 100 fabricated as described above.

Figure 18:
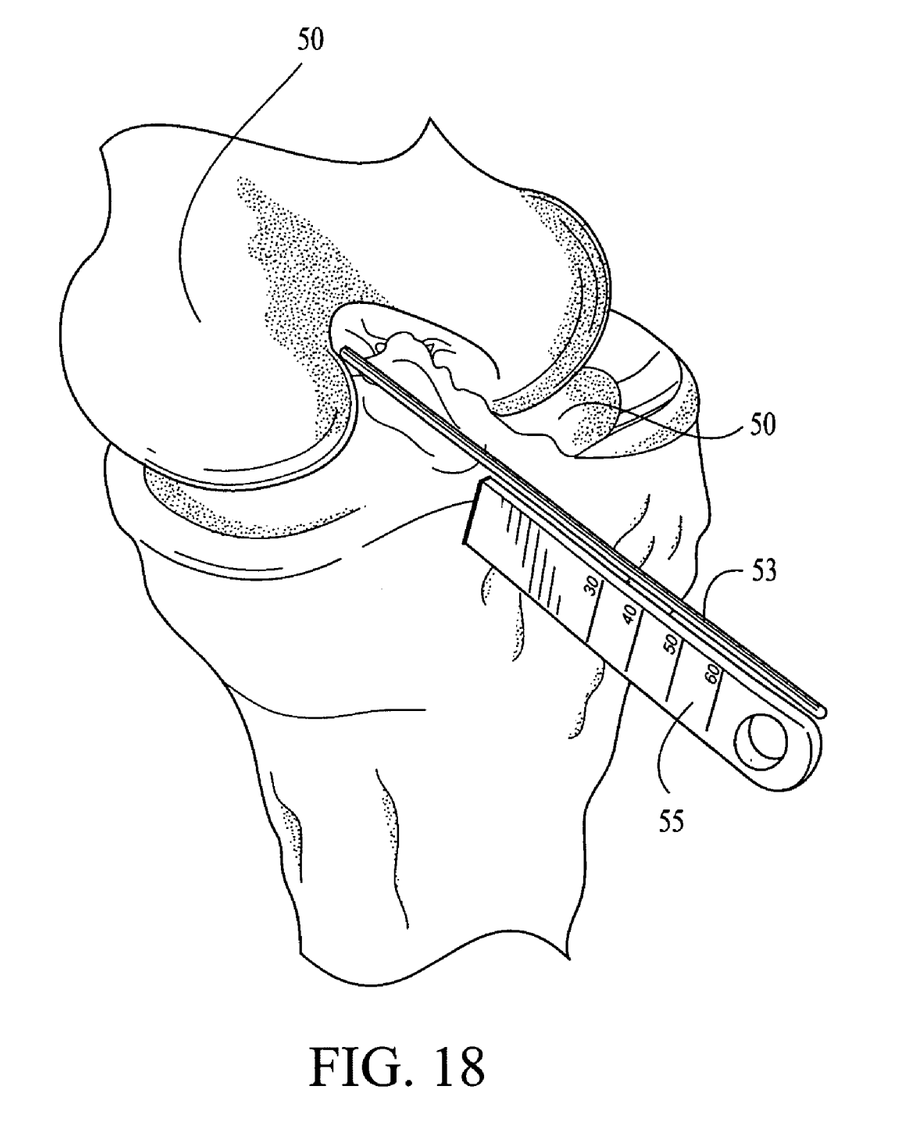
FIG. 18 illustrates a tibia for forming a dovetail tibial groove that accommodates the dovetail allograft implant of FIGS. 15–17.
Figure 19:
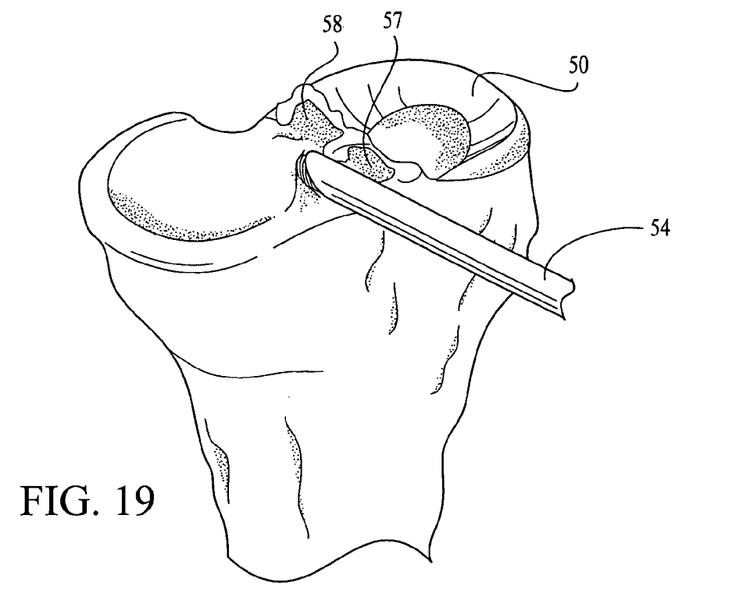
FIG. 19 illustrates a method of forming a dovetail tibial groove that accommodates the dovetail allograft implant of FIGS. 15–17 according to the present invention and at an initial stage of formation.
Figure 20:
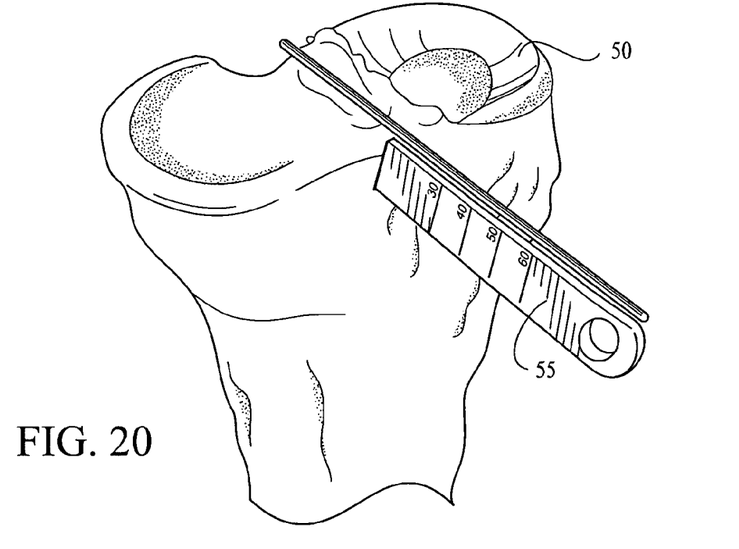
FIG. 20 illustrates the dovetail tibial groove of the present invention at a stage of formation subsequent to that shown in FIG. 19.
Figure 21:
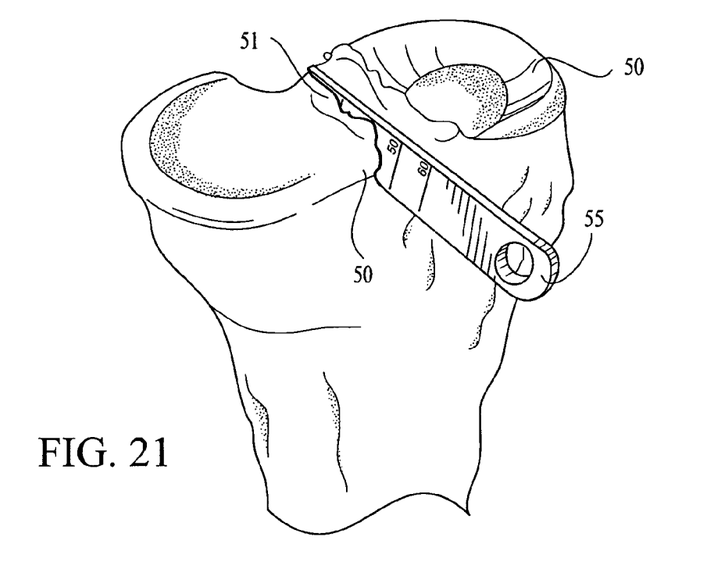
FIG. 21 illustrates the dovetail tibial groove of the present invention at a stage of formation subsequent to that shown in FIG. 20.

Osteotome 55 and alignment guide 53 are assembled, as shown in FIG. 18, after debriding the remaining meniscus just to the periphery, leaving only a thin cartilaginous peripheral rim attached to the capsule. Using a high speed bur, the lateral tibial eminence is shaved down until there is a bleeding vascular bed. Removal of the tibial eminence enhances exposure and ensures proper placement of the drill guide, as described in more detail below. Alignment rod 54 (FIG. 19) is then positioned in an anterior to posterior plane, entered through the anterior and posterior horns 57 and 58, respectively, of the tibial meniscus. FIG. 20 illustrates osteotome 55 and alignment rod 54 positioned so that the osteotome 55 can advance into the proximal side of tibia 50 through the horns 57, 58 so that the top of the osteotome 55 is flush with tibial plateau 51 and stops at the posterior horn 58, as shown in FIG. 21.

Figure 22:
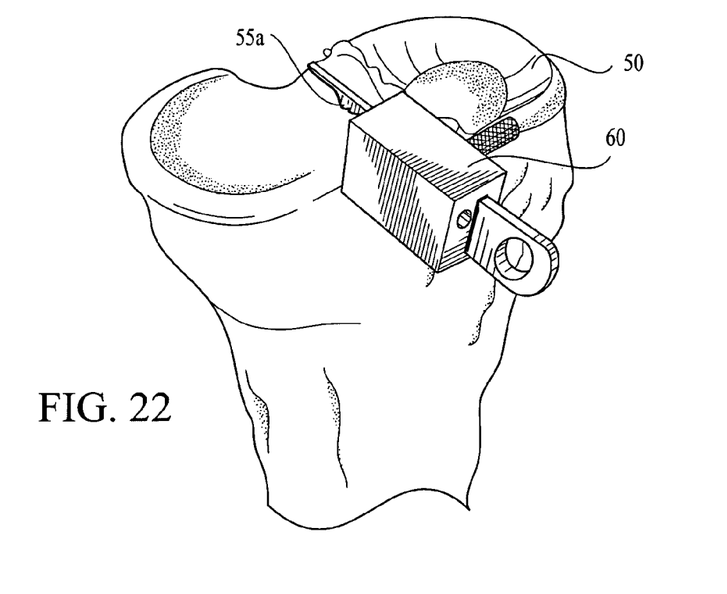
FIG. 22 illustrates the dovetail tibial groove of the present invention at a stage of formation subsequent to that shown in FIG. 21.
Figure 23:
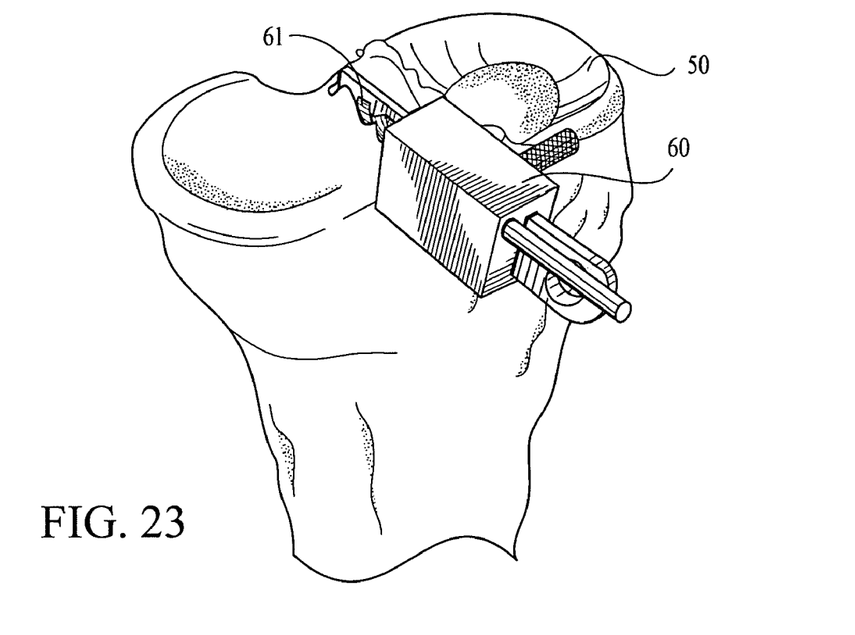
FIG. 23 illustrates the dovetail tibial groove of the present invention at a stage of formation subsequent to that shown in FIG. 22.
Figure 24:
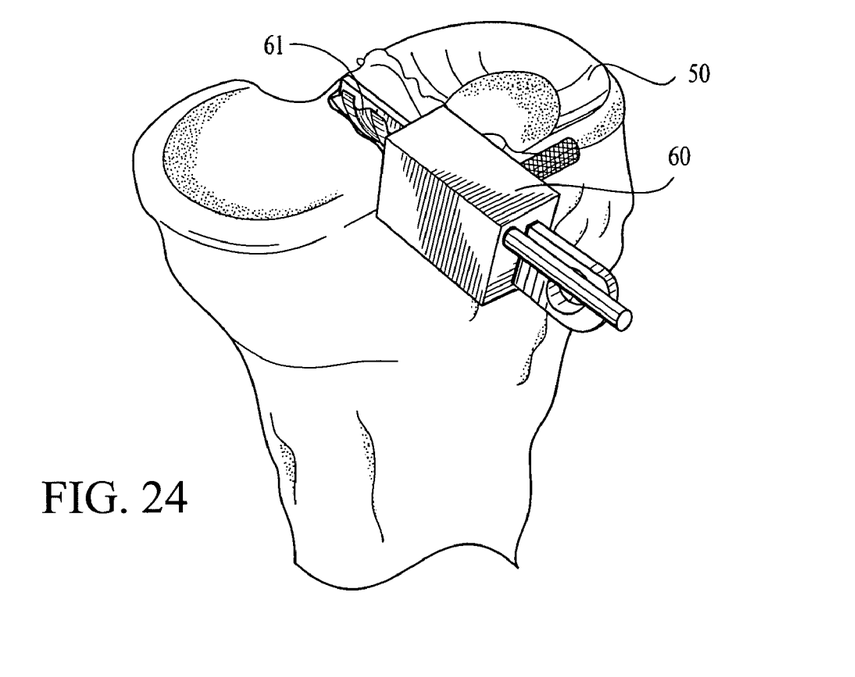
FIG. 24 illustrates the dovetail tibial groove of the present invention at a stage of formation subsequent to that shown in FIG. 23.

The handle of osteotome 55 is then removed, leaving its blade 55a into position. A first Drill Guide 60 is subsequently positioned over the blade 55a, flush to the anterior tibia, as shown in FIG. 22. Using a 6 mm drill bit 61 (FIG. 23), the tibial plateau 51 is cut through and drilled through the first Drill Guide 60, from the anterior horn 57 to the posterior horn 58 for a distance "L" which illustrates the length of the dovetail meniscal implant 100 (FIG. 17). FIG. 24 illustrates the 6 mm drill bit 61 cutting through the plateau channel and advancing through into the tibia under direct visualization until it contacts the posterior tibial cortex.

Figure 25:
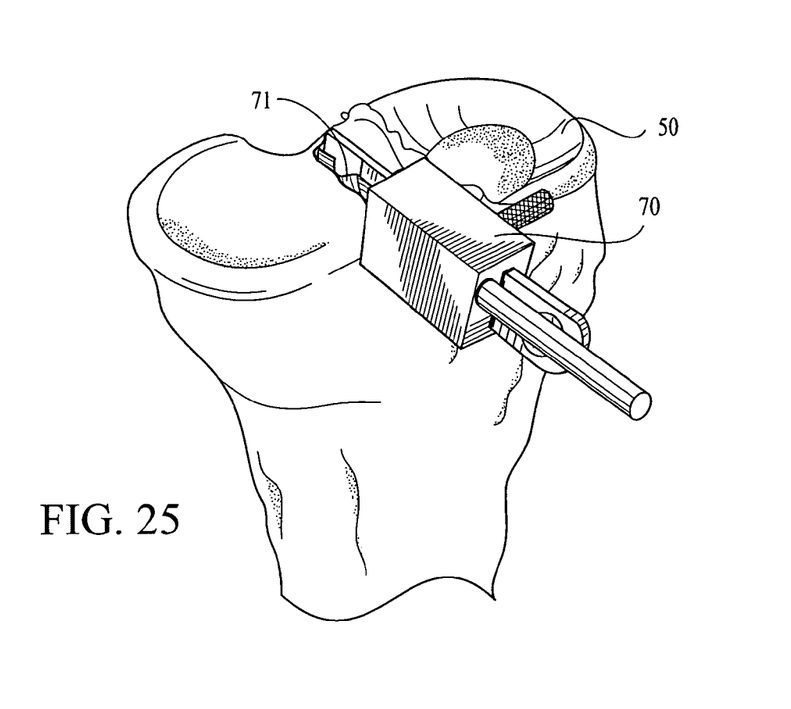
FIG. 25 illustrates the dovetail tibial groove of the present invention at a stage of formation subsequent to that shown in FIG. 24.
Figure 26:
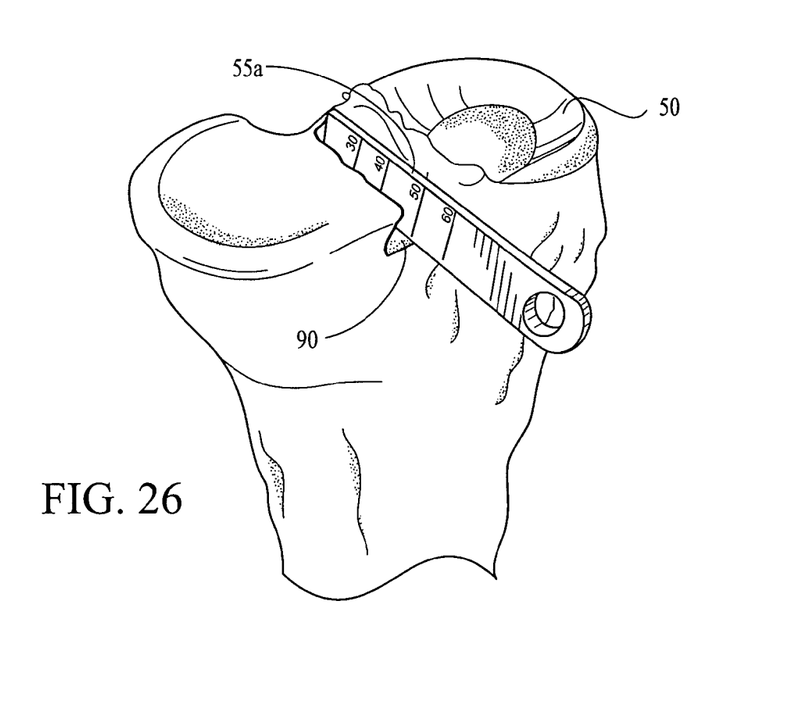
FIG. 26 illustrates the dovetail tibial groove of the present invention at a stage of formation subsequent to that shown in FIG. 25.

The first Drill Guide 60 that accommodates the 6 mm drill bit 61 is then removed from the osteotome 55, so that a second Drill Guide 70 is attached to the osteotome 55, as shown in FIG. 25. The second Drill Guide 70 accommodates an 8 mm drill bit 71 (FIG. 25) to drill through the tibial plateau 51 from the anterior horn 57 to the posterior horn 58, in a way similar to that using the 6 mm drill bit 61. A curette may be optionally used to further debride the groove subsequent to the drilling operation. FIG. 26 illustrates tibial groove 90 formed within tibia 50 at the end of the drilling operation with both the 6 mm drill bit 61 and 8 mm drill bit 71.

Figure 27:
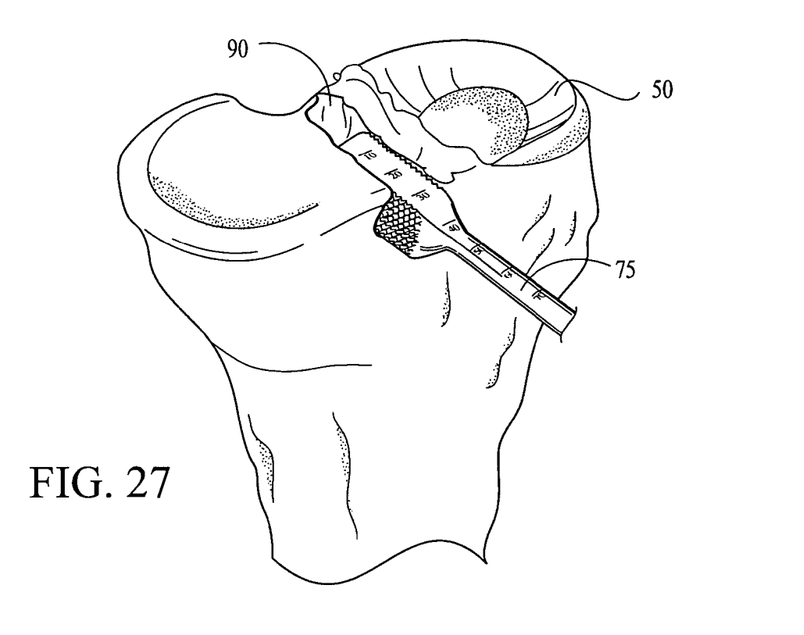
FIG. 27 illustrates the dovetail tibial groove of the present invention at a stage of formation subsequent to that shown in FIG. 26.
Figure 28:
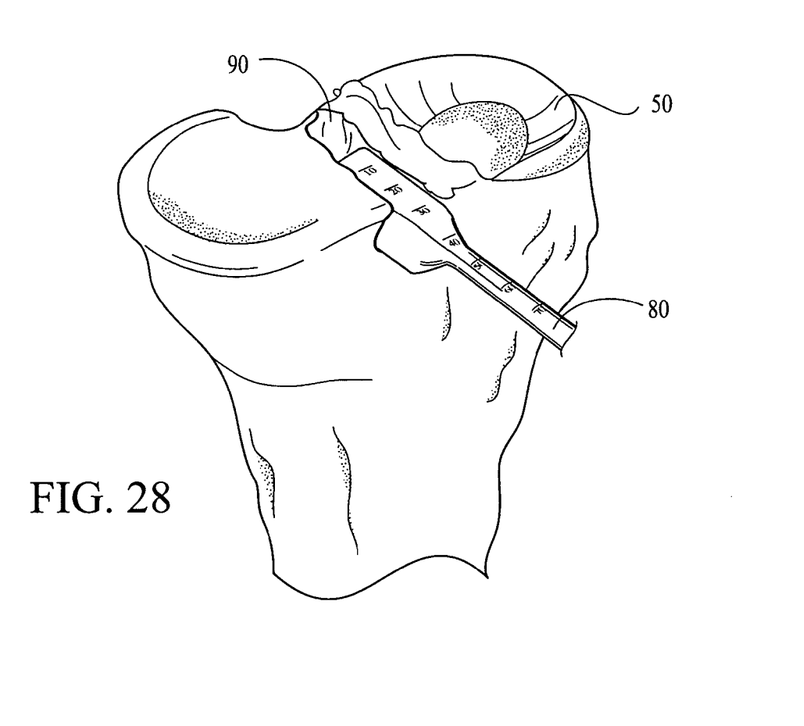
FIG. 28 illustrates the dovetail tibial groove of the present invention at a stage of formation subsequent to that shown in FIG. 27.
Figure 29:
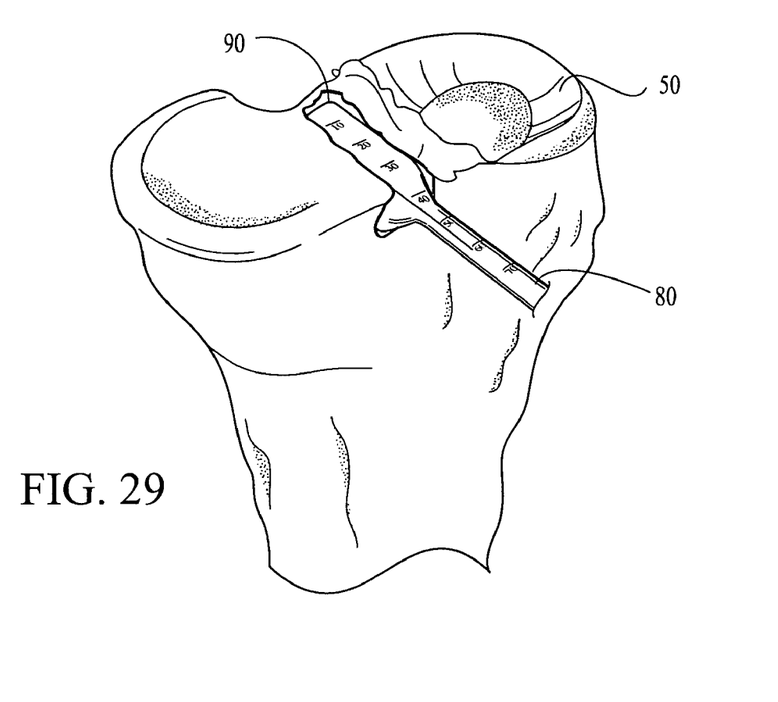
FIG. 29 illustrates the dovetail tibial groove of the present invention at a stage of formation subsequent to that shown in FIG. 28.
Figure 30:
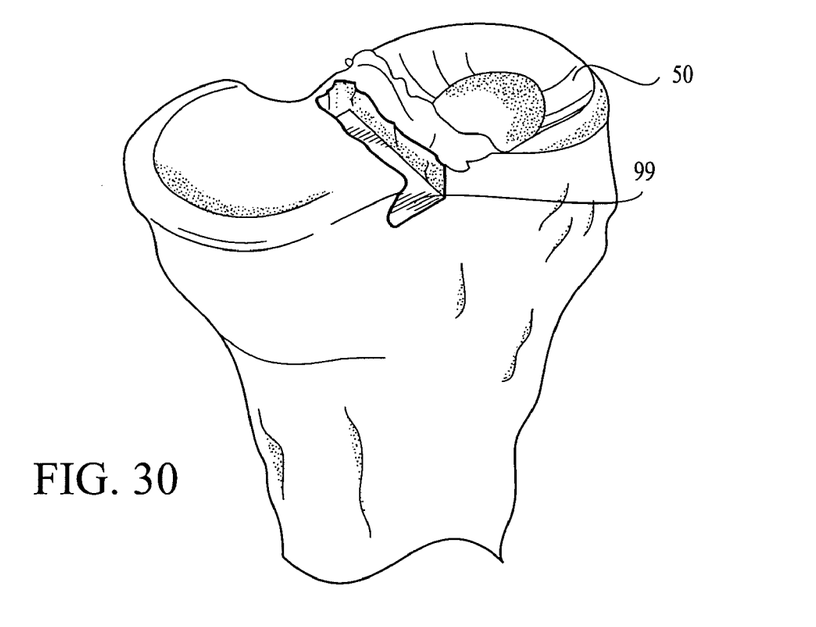
FIG. 30 illustrates the dovetail tibial groove of the present invention at a stage of formation subsequent to that shown in FIG. 29.

A rasp 75 is subsequently used to create the orthogonal angle of the dovetail configuration A (FIGS. 15, 16 and 17) into the tibial groove 90, as shown in FIG. 27. The rasp 75 must remain flush to the articular surface of the tibia and may be slowly advanced with a combination of maletting and hand rasping until it reaches the posterior tibial cortex. A dilatator 80 (FIGS. 28, 29) may be also inserted in the tibial groove 90 to increase the size of the drilled channel and to form the dovetail acute angle α of the dovetail configuration A (FIGS. 15, 16 and 17), using gentle taps of a mallet if necessary, and to complete the formation of the longitudinal dovetail tibial groove 99, as shown in FIGS. 30 and 31.

The longitudinal dovetail tibial groove 99 has a size and a length "L" that accommodate the dovetail meniscal allograft implant 100 fabricated as described above. By placing a ruler inside the prepared tibial groove 99, the length L is properly measured and then transferred onto the allograft bone block 14 of FIG. 1, to prepare the formation of the dovetail meniscal allograft implant 100, as described above with reference to FIGS. 15–17.

Finally, the dovetail meniscal allograft implant 100 is passed into the recipient dovetail tibial groove 99, as shown in FIG. 32, and the dovetail groove is cleared of any remaining bone debris in the posterior portion of the tibia. As the dovetail meniscal allograft implant 100 is delivered to the tibial groove 99, the graft passing suture attached to the meniscal allograft implant 100 is lead out the posterior lateral capsule via a standard inside out meniscal suturing technique. A meniscal allograft tamp may be employed to position the meniscal allograft implant 100 into the dovetail tibial groove 99.

As described above, the invention provides an improvement over the "keyhole" technique in that the shapes of the dovetail meniscal allograft implant 100 and of the corresponding longitudinal dovetail tibial groove 99 are more easily reproducible compared to the "keyhole" structures. Further, the invention provides a method of fabricating a meniscal allograft implant, such as the dovetail meniscal allograft implant 100, in about 5 to 8 minutes, as opposed to about 45 minutes required for the fabrication of the "keyhole" allograft structure.

Variations, modifications, and other uses of the present invention will become apparent to those skilled in the art, including the following, non-limiting examples: attachment of bone to bone; attachment of soft tissue to bone; non-medical applications. Thus, although the present invention has been described in relation to particular embodiments thereof, many other variations and modifications and other uses will become apparent to those skilled in the art.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of surgery, comprising the steps of:
   forming a bone groove having a trapezoidal cross-section in a tibial plateau using an osteotome which is aligned and advanced into the tibial plateau, a first drill guide which is received over the osteotome and guides a first drill bit for drilling through a first portion of the tibial plateau, and a second drill guide which is received over the osteotome and guides a second drill bit for drilling through a second portion of the tibial plateau; and
   installing a single piece mensical allograft formed of a correspondingly shaped trapezoidal bone block and a meniscus into the bone groove, wherein the trapezoidal bone block of the meniscal allograft is formed by making three cuts of the bone block using a workstation and three cutting jigs, such that the bone block of the meniscal allograft has two edges that define a ninety degree angle, and two edges that define an acute angle.

2. The method of claim 1, wherein the acute angle is about 25 degrees to about 75 degrees.

3. The method of claim 1, wherein the acute angle is about 45 degrees.

4. A method of performing orthopaedic surgery, the method comprising the steps of:
   forming a longitudinal groove into a tibial plateau, the longitudinal groove having a trapezoidal cross-section and a predefined length, the longitudinal groove being formed using an osteotome which is aligned and advanced into the tibial plateau, a first drill guide which is received over the osteotome and guides a first drill bit for drilling through a first portion of the tibial plateau, and a second drill guide which is received over the osteotome and guides a second drill bit for drilling through a second portion of the tibial plateau; and
   installing into the longitudinal groove an elongated single piece meniscal allograft implant formed of a bone block with a meniscus, the bone block having a trapezoidal cross-section corresponding to the shape of the longitudinal groove, wherein the bone block of the meniscal allograft is formed into a trapezoidal cross section by mounting the allograft onto a work station and making three cuts into the bone block using a workstation and three cuffing jigs.

\* \* \* \* \*